United States Patent [19]

Inoue et al.

[11] 4,201,844
[45] May 6, 1980

[54] PROCESS FOR PRODUCING A HYDROXYFATTY ACID ESTER

[75] Inventors: Shigeo Inoue, Saitama; Norioki Miyamoto, Yokkaido, both of Japan

[73] Assignee: Kao Soap Company, Limited, Tokyo, Japan

[21] Appl. No.: 928,867

[22] Filed: Jul. 28, 1978

[30] Foreign Application Priority Data

Aug. 1, 1977 [JP] Japan .................................. 52/92427

[51] Int. Cl.$^2$ ................................................. C12P 7/62
[52] U.S. Cl. ...................... 435/135; 435/944; 260/410.6
[58] Field of Search ...................... 260/410.6; 195/3 R, 195/12, 30

[56] References Cited

U.S. PATENT DOCUMENTS

| | | | |
|---|---|---|---|
| 3,312,684 | 4/1967 | Spencer et al. | 195/30 X |
| 3,445,337 | 5/1969 | Spencer et al. | 195/30 X |
| 3,483,083 | 12/1969 | Elson et al. | 195/30 |

FOREIGN PATENT DOCUMENTS 45-947  1/1970  Japan .

*Primary Examiner*—John F. Niebling

*Attorney, Agent, or Firm*—Oblon, Fisher, Spivak, McClelland & Maier

[57] ABSTRACT

A process for producing a hydroxyfatty acid polyhydric alcohol ester, which comprises; adding at least one polyhydric alcohol represented by the formula (III) or (IV),

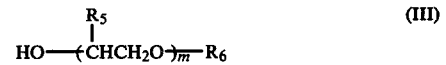

or

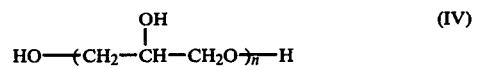

wherein $R_5$ represents a hydrogen atom or a methyl group, $R_6$ represents a hydrogen atom or an alkyl group having 1 to 5 carbon atoms, and m and n represent integers from 1 to 6, to hydrated Sophorolipid which is a fermentation product of Torulopsis bombicola; distilling off water under reduced pressure; and subjecting the resulting mixture to an alcoholysis reaction by adding an acid catalyst to the mother liquor.

7 Claims, No Drawings

PROCESS FOR PRODUCING A HYDROXYFATTY ACID ESTER

BACKGROUND OF THE INVENTION

1. Field of the Invention

This invention relates to a process for producing a hydroxyfatty acid polyhydric alcohol ester from Sophorolipid which is a fermentation product of Torulopsis bombicola.

2. Description of the Prior Art

It has been reported by J. F. T. Spencer et al [Canadian Journal of Chemistry, 39, 846 (1961)] that a great quantity of Sophorolipid is produced in a fermentation liquid by culturing Torulopsis bombicola.

Sophorolipid is a mixture of the compounds represented by the formulae (I) and (II),

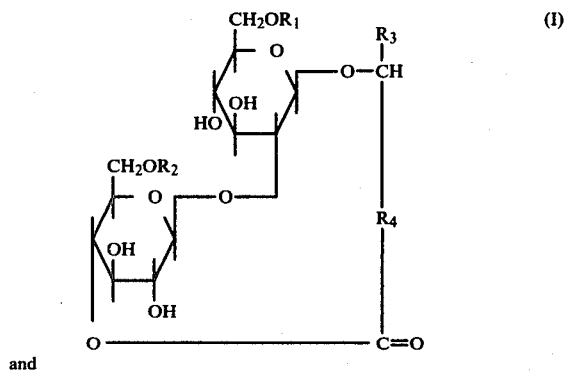

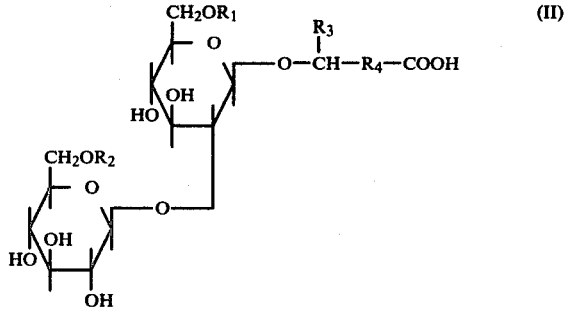

I-a: $R_1 = R_2 = COCH_3$

I-b: $R_1 = COCH_3$, $R_2 = H$

I-c: $R_1 = H$, $R_2 = COCH_3$

I-d: $R_1 = R_2 = H$

II-a: $R_1 = R_2 = COCH_3$

II-b: $R_1 = COCH_3$, $R_2 = H$

II-c: $R_1 = H$, $R_2 = COCH_3$

II-d: $R_1 = R_2 = H$ wherein $R_3$ represents H or $CH_3$, and $R_4$ represents a saturated or unsaturated hydrocarbon group having 11 to 15 carbon atoms when $R_3$ is $CH_3$.

As is clear from the above formulae, Sophorolipid contains a hydroxyfatty acid having a hydroxy group at the ω or ω-1 position in its structure, which can not be synthesized without much difficulty. This hydroxyfatty acid can be used as a raw material for a large ring lactone musk possessing a musky perfume which is highly valued. In fact, various attempts have been made to produce the hydroxyfatty acid by synthetic means, and many reports on this problem have been made public. However, these known synthetic methods are industrially unacceptable because of difficult availablity of raw materials, complexity of processes and difficult processing. As a result, such large ring lactone musk is now marketed as an expensive perfume.

If the hydroxyfatty acid for synthesizing the large ring lactone musk can be produced from Sophorolipid such a process is industrially superior because a great deal of Sophorolipid is economically available by a fermentation method.

Deacylation of Sophorolipid has been reported as a process for producing a hydroxyfatty acid using Sophorolipid as a raw material (Japanese Patent Publication No. 45-947). According to this report, the thus obtained hydroxypalmitic acid is lactonized to give a large ring lactone musk which is obtained at a cost as low as 1/20 of that by any conventional synthetic method.

This process contains the steps of producing the hydroxypalmitic acid from Sophorolipid, reacting this acid with glycerine to produce a hydroxyfatty acid ester or hydroxyfatty acid polymer, and obtaining a large ring lactone musk by ester interchange.

This process involves the following complicated steps:

(1) Hydrolyzing Sophorolipid with the use of an acid or alkali.

(2) Extracting hydroxypalmitic acid with an organic solvent.

(3) Separating the aqueous layer containing glucoside.

(4) Concentrating the organic solvent layer.

(5) Fractionally crystallizing the hydroxypalmitic acid by recrystallization of the extract in the organic solvent.

(6) Producing an intermediate for a large ring lactone musk by esterification or polymerization of the hydroxypalmitic acid.

The present inventors have examined a wide variety of processes for producing a large ring lactone musk in order to eliminate the shortcomings of the conventional process and have succeeded in producing a hydroxyfatty acid ester from Sophorolipid for a raw material for use as synthesizing a large ring lactone. Sophorolipid produced by fermentation can be obtained only in a hydrated form by any separating means. Sophorolipid has a viscosity of more than 100,000 cps in its dehydrated form at room temperature and more than 20,000 cps even at 80° C. Therefore, it is nearly impossible to dehydrate Sophorolipid on an industrial basis. Accordingly, the hydrous system is indispensable in order to yield a hydroxyfatty acid from Sophorolipid by hydrolysis. The present inventors have made many studies concerning lowering the viscosity of Sophorolipid in order to obtain dehydrated Sophorolipid and produce a hydroxyfatty acid derivative directly from Sophorolipid. As a result of these studies, they have found that particular polyhydric alcohols possess good miscibility with Sophorolipid and that the viscosity of Sophorolipid is significantly decreased by adding these polyhydric alcohols, which can act as esterifying agents with the hydroxyfatty acid.

Based on this finding, the present invention has been accomplished.

SUMMARY OF THE INVENTION

This invention provides a process for producing a hydroxyfatty acid polyhydric alcohol ester which comprises adding at least one polyhydric alcohol represented by the formulae (III) or (IV) to hydrated Sophorolipid which is a fermentation product of Torulopsis bombicola, distilling off water under reduced pressure and subjecting the resulting mixture to an alcoholysis reaction by adding an acid catalyst to the mother liquor.

DETAILED DESCRIPTION OF THE PREFERRED EMBODIMENTS

Suitable polyhydric alcohols which are useful in this invention are represented by the formulae (III) or (IV),

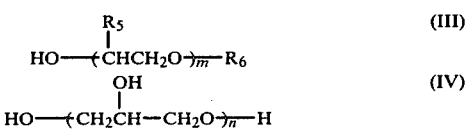

wherein $R_5$ represents a hydrogen atom or a methyl group, $R_6$ represents a hydrogen atom or an alkyl group having 1 to 5 carbon atoms, and m and n represent integers from 1 to 6.

The polyhydric alcohols include, for example, ethylene glycol, ethylene glycol monomethyl ether, ethylene glycol monoethyl ether, ethylene glycol monopropyl ether, diethylene glycol, diethylene glycol monomethyl ether, diethylene glycol monoethyl ether, diethylene glycol monobutyl ether, polyethylene glycol having an average molecular weight of 150 to 300, polypropylene glycol, dipropylene glycol, tripropylene glycol, tetrapropylene glycol, pentapropylene glycol, hexapropylene glycol, propylene glycol monomethyl ether, propylene glycol monoethyl ether, propylene glycol monobutyl ether, dipropylene glycol monomethyl ether, dipropylene glycol monoethyl ether, tripropylene glycol monomethyl ether, block copolymers of ethylene glycol and propylene glycol having an average molecular weight of 120 to 360 and the like as represented by the formula (III), and, for example, glycerine, polyglycerine and the like as represented by the formula (IV).

Sophorolipid which is useful in the invention is hydrated Sophorolipid obtained by fermenting Torulopsis bombicola by any conventional method.

In carrying out the invention, a polyhydric alcohol is first added to hydrated Sophorolipid, and water is then exhaustively distilled off by means of any conventional topping apparatus. At the same time, any impurities having an offensive smell and a lower boiling point which are contained in the raw material are distilled off. A 2 to 5% addition of the polyhydric alcohol in terms of its weight ratio to Sophorolipid is sufficient for the purpose of merely eliminating water and impurities having an offensive smell, and lowering the viscosity of Sophorolipid to a proper value. However, from the standpoint of the amount of esterifying agent for the hydroxyfatty acid, it is preferable to add 5% or more of the polyhydric alcohol. Although the maximum amount is not specifically limited, 10 to 100 moles per 1 mol of Sophorolipid are preferably used.

To the thus prepared polyhydric alcohol solution of Sophorolipid, from which are removed water and impurities having an offensive smell, an acid catalyst, is added and the resulting mixture is heated. Suitable acid catalysts which are useful in the invention include strongly acidic mineral acids such as hydrochloric acid, nitric acid, sulfuric acid and the like, and organic acids such as p-toluenesulfonic acid, acetyl chloride, propionyl chloride and the like. The acid catalysts are preferably added to the polyhydric alcohol solution of Sophorolipid in a concentration of 1 to 3%. The reaction is preferably conducted with stirring at 70° to 150° C. to afford a hydroxyfatty acid due to the cleavage of the glycosyl ether bond of Sophorolipid and to subsequently obtain a hydroxyfatty acid polyhydric alcohol ester through an alcoholysis reaction.

The thus obtained reaction mixture is extracted with a solvent which does not dissolve the polyhydric alcohol and glucoside nor the hydroxyfatty acid polyhydric alcohol ester and which is selected from the group consisting of benzene, chloroform, carbon tetrachloride, carbon disulfide, petroleum ether, ethyl acetate and the like, thus yielding the hydroxyfatty acid polyhydric alcohol ester in a high yield of 90 to 95%. The hydroxyfatty acid polyhydric alcohol ester can be employed, for instance, as a raw material for synthesizing a large ring lactone musk.

The thus obtained hydroxyfatty acid polyhydric alcohol ester is represented by the formula (V),

wherein $R_3$ and $R_4$ are the same as defined above, and X represents

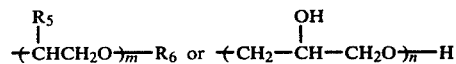

wherein $R_5$, $R_6$, m and n are the same as defined above.

The hydroxyfatty acid polyhydric alcohol ester can be converted to a large ring lactone musk which is a principal perfume constituent having a musky perfume, for instance, by lactonization according to the method disclosed in British Pat. No. 490,044.

As above described in detail, according to the invention, the hydroxyfatty acid polyhydric alcohol ester can be produced directly from a crude substance containing Sophorolipid obtained by fermentation in a good yield and a high purity, while omitting the step of preparing the hydroxyfatty acid which is essential in the conventional process. The present process is extremely superior and industrially acceptable.

The invention is illustrated below in further detail with reference to some non-limiting Examples.

EXAMPLE 1

(1) To a mixture of 1500 g of glucose, 75 g of a yeast extract and 15 g of urea was added water to adjust the whole volume to 15 l, and the resulting mixture was sterilized and used as a fermentation liquid. To 500 ml of this fermentation liquid was inoculated Torulopsis bombicola which had been cultured on the slant in the YM agar culture medium, and the mixture was cultured with shaking at 30° C. for 48 hours. After observing a sufficient growth of microorganisms, the mixture was poured into a fermentor previously prepared, and the fermentation was initiated. The fermentation was carried out under the following conditions: temperature, 18° C.; stirring, 300 rpm; and aeration, 0.33 VVM. The fermentation was first conducted for 24 hours after inoculation of the microorganisms, and palmitic acid was added in a ratio of 10 g/l and then added in the same ratio at intervals of 24 hours. The added palmitic acid amounted to 900 g. After the final addition, the fermentation was continued for 24 hours. The fermentation time totaled 168 hours. A Sophorolipid layer precipitating at the bottom of the fermentor was collected by decantation to give about 1700 g of a Sophorolipid solution having a viscosity of 1800 cps at 30° C. (measured by a B-type viscosimeter) and having a water content of about 45%.

(2) 100 g of the Sophorolipid solution was placed in a 300 ml flask, and 50 g of ethylene glycol was added to this solution. The mixture was evaporated with stirring at 100° C. in an oil bath under a reduced pressure of 250 mmHg to eliminate water. 60 minutes later, the distillation of water was completed, and the water content at this time was found to be less than 0.5%.

(3) About 2% of hydrochloric acid gas was passed into the thus obtained ethylene glycol solution of Sophorolipid, and the resulting mixture was reacted at 110° C. for 6 hours. After being allowed to cool to room temperature, the mixture was extracted with 200 ml of ethyl acetate to give 23.5 g (about 90% yield on the basis of the hydroxyfatty acid).

The infrared absorption spectra of this product indicated a peak at 1740 cm$^{-1}$ due to the ketone group of the ester bond, and a peak at 3600-3500 cm$^{-1}$ due to the hydroxy group. Four peaks were given by gas chromatography (1.5% FFAP-Chromosorb W 3 mm×1 m glass column, 200°-250° C.). Gas chromatography-mass spectrometry, under the same conditions of gas chromatography as above noted, indicated m/e 317 [M+H]$^+$, 313 [MH—H$_2$O]$^+$, 255 [M—OCH$_2$CH$_2$OH]$^+$. From these results, the product was ascertained to be HOCH$_2$(CH$_2$)$_{14}$COOCH$_2$CH$_2$OH and CH$_3$CH(OH)(CH$_2$)$_{13}$COOCH$_2$CH$_2$OH. Further, from the fact that m/e 341 [M—H]$^+$ was observed, the product was ascertained to contain HOCH$_2$(CH$_2$)$_7$CH=CH(CH$_2$)$_7$COOCH$_2$CH$_2$OH and CH$_3$CH(OH)(CH$_2$)$_6$CH=CH(CH$_2$)$_7$COOCH$_2$H$_2$OH.

EXAMPLE 2

In the same manner as in Example 1, 65 g of propylene glycol was added to Sophorolipid in a molar ratio of 10 of propylene glycol to Sophorolipid to prepare a propylene glycol solution of Sophorolipid. To this solution was added acetyl chloride in an amount of 3%, and the mixture was reacted at 120° C. for 5 hours. After being allowed to cool to room temperature, the mixture was extracted with carbon tetrachloride to give 25.5 g of the extract (92% yield on the basis of the hydroxyfatty acid).

The infrared absorption spectra of this product indicated a peak at 1740 cm$^{-1}$ due to the ketone group of the ester bond and a peak at 3600-3500 cm$^{-1}$ due to the hydroxy group. Four peaks were given by gas chromatography (under the same conditions as in Example 1). Gas chromatography-mass spectrometry indicated m/e 331 [M+H]$^+$, 313 [MH—H$_2$O]$^+$, 255 [M—OCH$_2$CH(OH)CH$_3$]$^+$. From these results, the product was ascertained to be HOCH$_2$(CH$_2$)$_{14}$COOCH$_2$CH(OH)CH$_3$ and CH$_3$CH(OH)(CH$_2$)$_{13}$COOCH$_2$CH(OH)CH$_3$. Further, from the fact that m/e 355 [M—H]$^+$ was observed, the product was ascertained to contain HOCH$_2$(CH$_2$)$_7$CH=CH(CH$_2$)$_7$COOCH$_2$CH(OH)CH$_3$ and CH$_3$CH)H(CH$_2$)$_6$CH=CH(CH$_2$)$_7$COOCH$_2$CH(OH)CH$_3$.

EXAMPLE 3

In the same manner as in Example 1, 80 g of glycerine was added to Sophorolipid in a molar ratio of 10 of glycerine to Sophorolipid to prepare a Sophorolipid-glycerine solution. To this solution was added nitric acid in an amount of 3%, and the mixture was reacted at 120° C. for 6 hours. After being allowed to cool to room temperature, the mixture was extracted with benzene to give 25.6 g of the extract (about 89% yield on the basis of the hydroxyfatty acid).

The infrared absorption spectra of this product indicated a peak at 1740 cm$^{-1}$ due to the ketone group of the ester bond and a peak at 3600-3500 cm$^{-1}$ due to the hydroxy group. A trimethylsilyl ether derivative of this product obtained with a silylating agent showed four peaks by gas chromatography (under the same conditions as in Example 1). Gas chromatography-mass spectrometry indicated m/e 562 [M]$^+$. From this result, the derivative was ascertained to be the trimethylsilyl ether of HOCH$_2$(CH$_2$)$_{14}$COOCH$_2$CH(OH)CH$_2$OH and CH$_3$CH(OH)(CH$_2$)$_{13}$COOCH$_2$CH(OH)CH$_2$OH.

Further, from the fact that m/e 588 [M]$^+$ was observed, the derivative was ascertained to contain the trimethylsilyl ether of HOCH$_2$(CH$_2$)$_7$CH=CH(CH$_2$)$_7$COOCH$_2$CH(OH)CH$_2$OH and CH$_3$CH(OH)(CH$_2$)$_6$CH=CH—(CH$_2$)$_7$COOCH$_2$CH(OH)CH$_2$OH.

EXAMPLE 4

To 20 g of the hydroxyfatty acid-glycerine ester obtained in Example 3 was added 0.2 g of sodium methoxide. The mixture was distilled under vacuum at 180° C. with dropwise addition of glycerine to give a large ring lactone product. The reaction time was 6 hours. The product was extracted with a solvent system of water and ethyl acetate, and the extract was fractionally distilled to give 85.5% of 1,16-hexadecanolide and 14.5% of 1,15-hexadecanolide. The product was a musky perfume-smelling substance.

What is claimed:

1. A process for producing an hydroxyfatty acid polyhydric alcohol ester, which comprises; adding at least one polyhydric alcohol represented by the formula (III) or (IV),

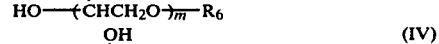

wherein R$_5$ represents a hydrogen atom or a methyl group, R$_6$ represents a hydrogen atom or an alkyl group having 1 to 5 carbon atoms, and m and n represent integers from 1 to 6, to hydrated Sophorolipid which is a fermentation product of *Torulopsis bombicola;* removing water by distillation under reduced pressure whereby a mother liquor is generated; and subjecting the resulting mixture to an alcoholysis reaction by adding an acid catalyst to the mother liquor.

2. A process according to claim 1, wherein $R_5$ is a hydrogen atom or a methyl group, $R_6$ is a hydrogen atom, m is 1 to 4, and n is 1 in the formula (III) or (IV).

3. A process according to claim 1 or 2, wherein said polyhydric alcohol is selected from the group consisting of ethylene glycol, propylene glycol, and glycerine.

4. A process according to any one of claims 1 or 2, wherein said acid catalyst is selected from the group consisting of hydrochloric acid, nitric acid, sulfuric acid, and p-toluenesulfonic acid.

5. A process according to any one of claim 1 or 2, wherein said polyhydric alcohol is added to Sophorolipid in a ratio of from 5 to 100 in terms of the molar ratio of the hydroxyfatty acid to Sophorolipid.

6. A process according to claim 3, wherein said acid catalyst is selected from the group consisting of hydrochloric acid, nitric acid, sulfuric acid, and p-toluenesulfonic acid.

7. A process according to claim 3, wherein said polyhydric alcohol is added to Sophorolipid in a ratio of from 5 to 100 in terms of the molar ratio of the hydroxyfatty acid to Sophorolipid.

* * * * *